United States Patent
McCabe

(10) Patent No.: US 8,277,741 B2
(45) Date of Patent: Oct. 2, 2012

(54) ANTI-GERMICIDAL AND/OR ANTIMICROBIAL APPARATUS FOR REDUCING AND/OR ELIMINATING GERMS AND/OR BACTERIA FROM THE SOLES OF FOOTWEAR AND METHOD FOR USE

(76) Inventor: Colin Adam McCabe, New York, NY (US)

(*) Notice: Subject to any disclaimer, the term of this patent is extended or adjusted under 35 U.S.C. 154(b) by 506 days.

(21) Appl. No.: 12/260,088

(22) Filed: Oct. 28, 2008

(65) Prior Publication Data

US 2010/0104470 A1    Apr. 29, 2010

(51) Int. Cl.
*B01J 19/12* (2006.01)
*F01N 3/20* (2006.01)
*A61L 2/00* (2006.01)

(52) U.S. Cl. ........ 422/186.3; 422/22; 422/105; 422/116

(58) Field of Classification Search .................. 422/105, 422/116, 186.3, 22
See application file for complete search history.

(56) References Cited

U.S. PATENT DOCUMENTS

| | | |
|---|---|---|
| 2,173,528 A | 9/1939 | Beale |
| 3,526,015 A | 9/1970 | Nappi |
| 3,940,820 A | 3/1976 | Smolka |
| 4,014,060 A | 3/1977 | Taylor |
| 4,118,818 A | 10/1978 | Holleran |
| 4,190,919 A | 3/1980 | Burford |
| 4,280,244 A | 7/1981 | Spirig |
| 4,358,867 A | 11/1982 | Berta |
| 4,411,931 A | 10/1983 | Duong |
| 4,432,112 A | 2/1984 | Muller et al. |
| 4,533,583 A | 8/1985 | May |
| 4,817,707 A | 4/1989 | Aoyama et al. |
| 4,918,778 A | 4/1990 | Chupin et al. |
| 5,028,468 A | 7/1991 | Taylor |
| 5,714,119 A | 2/1998 | Kawagoe et al. |

(Continued)

FOREIGN PATENT DOCUMENTS

EP    0513449    11/1992

(Continued)

OTHER PUBLICATIONS

English Translation of Japanese Document No. JP 10052480 provided by the Industrial Property Digital Library: Kato, Okada; Sterilisation door mat for patients used in hospital has material displaced by foot pressure to allow permeation of ultraviolet light for disinfecting foot; Feb. 24, 1998; http://www.ipdl.inpit.go.jp/homepg_e.ipdl.*

(Continued)

*Primary Examiner* — Kevin Joyner
(74) *Attorney, Agent, or Firm* — Dorsey & Whitney LLP

(57) ABSTRACT

The present invention relates an apparatus that reduces and/or eliminates germs and/or bacteria from the soles of a person's footwear, and an associated method of use. According to an exemplary embodiment of the present invention, a person can step onto and stand on the exemplary apparatus to have germs and/or bacteria reduced and/or eliminated from the soles of his or her footwear through the use of anti-germicidal and/or antimicrobial radiation and/or light. An exemplary apparatus according to an exemplary embodiment of the present invention can be configured so that when a person stands on a top portion, the person's footwear sinks to a bottom portion that is substantially transparent, displacing substantially opaque gel so that at least one of the soles of the person's footwear is exposed to the anti-germicidal and/or antimicrobial radiation and/or light source.

12 Claims, 3 Drawing Sheets

U.S. PATENT DOCUMENTS

| | | | |
|---|---|---|---|
| 5,771,528 A | 6/1998 | Nappi, Sr. | |
| 5,820,821 A * | 10/1998 | Kawagoe et al. | 422/22 |
| 5,991,967 A | 11/1999 | Williams | |
| 6,067,688 A | 5/2000 | West | |
| 6,233,776 B1 | 5/2001 | Blum et al. | |
| 6,258,736 B1 | 7/2001 | Massholder | |
| 6,290,809 B1 | 9/2001 | Bielfeldt et al. | |
| 6,406,549 B1 | 6/2002 | Berg et al. | |
| 6,417,778 B2 | 7/2002 | Blum et al. | |
| 6,458,442 B1 | 10/2002 | McKay | |
| 6,584,636 B2 | 7/2003 | Schlem | |
| 6,844,058 B2 | 1/2005 | Blum et al. | |
| 6,886,209 B2 | 5/2005 | Blum et al. | |
| 6,899,927 B2 | 5/2005 | Park et al. | |
| 6,972,416 B2 | 12/2005 | Huang et al. | |
| 7,024,721 B2 | 4/2006 | McKay | |
| 7,051,393 B2 | 5/2006 | Cox | |
| 2001/0004483 A1 | 6/2001 | Blum et al. | |
| 2002/0023308 A1 | 2/2002 | Blum et al. | |
| 2002/0028313 A1 | 3/2002 | Blum et al. | |
| 2002/0068147 A1 | 6/2002 | Blum et al. | |
| 2002/0071936 A1 | 6/2002 | Gentiluomo et al. | |
| 2002/0092110 A1 | 7/2002 | Blum et al. | |
| 2002/0121985 A1 | 9/2002 | Blum et al. | |
| 2002/0156634 A1 | 10/2002 | Blum et al. | |
| 2003/0024062 A1 | 2/2003 | McKay | |
| 2003/0135135 A1 | 7/2003 | Miwa et al. | |
| 2003/0135947 A1 | 7/2003 | McKay | |
| 2004/0221411 A1 | 11/2004 | Blum et al. | |
| 2005/0027029 A1 | 2/2005 | Park et al. | |
| 2006/0152483 A1 | 7/2006 | Blum et al. | |
| 2007/0044261 A1 | 3/2007 | Bolton | |
| 2007/0222633 A1 | 9/2007 | Blum et al. | |
| 2008/0057534 A1 * | 3/2008 | Martin et al. | 435/34 |
| 2008/0104782 A1 | 5/2008 | Hughes | |
| 2008/0113214 A1 | 5/2008 | Davis et al. | |
| 2008/0118395 A1 | 5/2008 | Benedek | |
| 2008/0179544 A1 | 7/2008 | Kaiser et al. | |
| 2008/0310996 A1 * | 12/2008 | Kim et al. | 422/24 |

FOREIGN PATENT DOCUMENTS

| | | |
|---|---|---|
| EP | 1212972 | 6/2002 |
| EP | 1308120 | 5/2003 |
| EP | 1659357 | 5/2006 |
| EP | 1775335 | 4/2007 |
| GB | 238634 | 8/1925 |
| GB | 2383197 | 6/2003 |
| GB | 2384703 | 8/2003 |
| GB | 2386833 | 10/2003 |
| JP | 2152432 | 6/1990 |
| JP | 10052480 A * | 2/1998 |
| JP | 200041701 | 2/2000 |
| JP | 2001224670 | 8/2001 |
| JP | 2002000706 | 1/2002 |
| JP | 2003033419 | 2/2003 |
| JP | 2003329258 | 11/2003 |
| JP | 200770799 | 3/2007 |
| KR | 20-1997-0016266 | 5/1997 |
| KR | 10-2003-0042850 | 6/2003 |
| KR | 10-2008-0048452 | 6/2008 |
| WO | 0065980 | 11/2000 |
| WO | 0178891 | 10/2001 |
| WO | 0180707 | 11/2001 |
| WO | 0216051 | 2/2002 |
| WO | 0217768 | 3/2002 |
| WO | 0238029 | 5/2002 |
| WO | 0249498 | 6/2002 |
| WO | 02065451 | 8/2002 |
| WO | 03039324 | 5/2003 |
| WO | 03053101 | 6/2003 |
| WO | 2004045362 | 6/2004 |
| WO | 2005045117 | 5/2005 |
| WO | 2005072115 | 8/2005 |
| WO | 2006019390 | 2/2006 |
| WO | 2006132852 | 12/2006 |
| WO | 2007027859 | 3/2007 |
| WO | 2007027871 | 3/2007 |
| WO | 2007051996 | 5/2007 |
| WO | 2007070185 | 6/2007 |
| WO | 2007070186 | 6/2007 |
| WO | 2007070520 | 6/2007 |
| WO | 2007078412 | 7/2007 |
| WO | 2007106835 | 9/2007 |
| WO | 2008084487 | 7/2008 |

OTHER PUBLICATIONS

"OSRAM Research Team Wins German Future Prize for LED Lighting Technology". Business Wire, Inc. <http://www.businesswire.com> Dec. 8, 2007.
"Clean lines for hospital design". Building Design. Apr. 22, 2005.
"Safety/Emergency Flashing LED Chevron Arrow Mat Operates for Nearly 48 Hours on 2 AA-Batteries". Jun. 20, 2005.
Dudley, Jennifer. "Hi-tech fabric promises room with a hue or few." The Courier Mail. Queensland, Australia. Sep. 8, 2005.
"Company Mops Up Hospital Deal". The Star. May 17, 2004.
"Preventive Measures to Stop the Spread of Foot and Mouth Disease". PR Newswire. Apr. 12, 2001.
Wise, Kathryn O. "The magic of carpet". Health Facilities Management. Apr. 1996.
Hill, Alma E. "Underfoot, a world that simply glows". Cox News Service. Oct. 5, 1999.
Tapping, Mary. "The light fantastic will help riders to stand out". Western Daily Press. Nov. 30, 2002.
"Solenium, an Interface Company, Chooses Shell CORTERA Fibers for New Flooring System Aimed at School, Health Care Markets". PR Newswire. Jul. 27, 1999.
"Solutions: Surfaces—Infinite variety". Building Design. Feb. 22, 2008.
"Sure-Foot Glow-in-the-Dark Message Stair Thread". Product News Network. Mar. 9, 2007.
Sellers, Kathryn. "Carpeting course". Health Facilities Management. Sep. 2001.
Ultraviolet Light Disinfection Scanner. Gold Violin.
International Search Report and Written Opinion for PCT/US/2009/062398 dated Jun. 8, 2010.

* cited by examiner

ANTI-GERMICIDAL AND/OR ANTIMICROBIAL APPARATUS FOR REDUCING AND/OR ELIMINATING GERMS AND/OR BACTERIA FROM THE SOLES OF FOOTWEAR AND METHOD FOR USE

FIELD OF THE INVENTION

The present invention relates to an apparatus that reduces and/or eliminates germs and/or bacteria from the soles of a person's footwear, and an associated method of use thereof. Particularly, the present invention relates to an apparatus onto which a person can step and stand to have germs and/or bacteria reduced and/or eliminated from the soles of his or her footwear through the use of anti-germicidal and/or antimicrobial light and/or radiation.

BACKGROUND INFORMATION

Preventing germs, bacteria, viruses, fungi and other pathogenic microbes (hereinafter together referred to as "pathogens") from entering a dwelling or building is both desirable and often necessary for reducing or eliminating infections and diseases from being contracted by people, which can cause them to become ill. People often repeatedly wash their hands to reduce or eliminate any pathogens that their hands may have come into contact with to thereby prevent such pathogens from infecting a person and causing them to become ill. However, a significant source of pathogens can be brought into a dwelling or building on a person's shoes, and more often more abundantly on the soles of a person's shoes. In some cultures, it has become traditional and expected for a person to remove their shoes before entering a dwelling or building where pathogens may be of particular concern, such as, e.g., a hospital or a restaurant. But in many other cultures, such tradition does not exist and/or has not been practiced. Thus, people tend to walk into a dwelling or building wearing their shoes without knowing of or being concerned about any dirt or pathogens that may be entering into the dwelling or building on the soles of their shoes.

Therefore, it has become common for people to place mats or rugs on either or both sides (e.g., inside and/or outside) of a door to a dwelling or building. However, such mats and rugs typically have been configured and used for removing dirt and debris from the soles of a person's shoes upon a person standing on the mat or rug and wiping their shoes on the mat. Such mats have been made of, e.g., rubber, straw or cloth, and include a course surface to help facilitate at least a partial removal of dirt and debris from the soles of a person's shoes. One apparent problem with these types of mats is that they would themselves become dirty and/or infected with pathogens, and therefore may likely have to be repeatedly cleaned and sanitized, often frequently depending on the amount of exposure to dirt and debris. However, dirt, debris and pathogens tend to build-up on mats of this type after just a single use. Thus, unless the mat is thoroughly cleaned and disinfected after each use, dirt and pathogens may be spread and tracked into the dwelling or building upon another person using the mat.

Accordingly, in addition to the aforementioned traditional types of mats, there have been introduced devices for cleaning the soles of shoes that purportedly minimize the amount of dirt and moisture brought into a building by persons entering the building. One device, for example, is described in U.S. Pat. No. 6,406,549. The device described in the publication uses a mat configured to rotate as an endless loop between guide rollers within a floor opening at an entranceway within a building. In one section, in which the mat runs in one direction, the mat acts as a tread surface to absorb dirt and moisture. In another section, the mat runs in the opposite direction, cleaned of the gathered dirt and moisture, and reconditioned by mechanical, hydraulic or pneumatic mechanisms within the floor opening. Another device, for example, which is described in U.S. Pat. No. 7,024,721, uses multiple removable and disposable cleaning sheets that are supported in a stacked configuration on an upper surface of a base sheet. Thus, when the top sheet becomes dirty or saturated, it can be removed and disposed of with the sheet that was immediately below it, which becomes the top sheet.

Another device, for example, which is described in U.S. Pat. No. 7,051,393, has been introduced to purportedly remove dirt and germs from a person's shoes before they enter a home or business. Four systems that are described in this publication are used, including (i) a first system that provides a method for initiating and replenishing fluids that contain a disinfectant; (ii) a second system that presents the method of providing a new dampened wiping surface each time the device is ready for use; (iii) a third system that provides a means of removing solid particulates from a used wiping surface; and a fourth system that provides the method of collecting the previously removed solids.

However, these types of mats are not specifically configured for substantially reducing or eliminating pathogens that may be on the soles of a person's footwear. Therefore, it appears that there is a need for apparatus and method that can significantly reduce and/or eliminate germs and/or bacteria from the soles of a person's shoes.

SUMMARY OF EXEMPLARY EMBODIMENTS

One of the objects of the present invention is to overcome the deficiencies commonly associated with the prior art a discussed above, and provide apparatus and method that can significantly reduce and/or eliminate germs and/or bacteria from the soles of a person's footwear.

According to one exemplary embodiment of the present invention, provided is an apparatus for reducing and/or eliminating germs and/or bacteria from at least one sole of a footwear of a subject. The exemplary apparatus can include, for example, a housing and a first particular part located within or coupled to the housing. The exemplary first particular part can include at least one radiation source, which can be exposed to irradiate the at least one sole when the subject applies force on the apparatus, for example. The exemplary radiation source(s) can be configured to emit an anti-germicidal radiation and/or an antimicrobial radiation. At least one of the exemplary anti-germicidal radiation and/or antimicrobial radiation can be an ultra-violet light and/or radiation, for example.

The exemplary apparatus can include a second particular part located at or near a top section of the housing. The exemplary second particular part can include a top portion, a bottom portion, and a gel disposed therebetween, for example. The exemplary bottom portion can be at least substantially transparent, and the exemplary gel can be at least substantially opaque. The exemplary apparatus can be structured so that the top portion sinks to the bottom portion so as to displace the gel under the subject's footwear when the subject steps onto the top portion, for example.

The exemplary radiation source(s) can be configured to automatically initiate an emission of the exemplary anti-germicidal radiation and/or antimicrobial radiation after a predetermined amount of time passes from a time when the subject applies force on the second particular part, for example. The exemplary radiation source(s) also can be configured to initiate an emission of the exemplary anti-germicidal radiation and/or antimicrobial radiation upon receiving a manual input from the subject, for example.

Additionally, the exemplary radiation source(s) can be configured to emit the exemplary anti-germicidal radiation and/or antimicrobial radiation until a signal to stop is received thereby, for example. The exemplary signal can be based upon at least one of time or an indication from a sensor provided in or coupled to the exemplary housing. The exemplary sensor can be configured to detect a level of pathogens residing on the soles of the subject's footwear, and provide an indication when a threshold level has been reached indicating the level of detected pathogens, for example. The exemplary radiation source(s) can be at least one of a radiation cone, UV light bulb and/or LED, for example.

According to another exemplary embodiment of the present invention, provided is an exemplary method for at least one of reducing or eliminating germs and/or bacteria from at least one sole of footwear of a subject. The exemplary method can include, for example, a subject applying force on an apparatus including at least one radiation source; and the radiation source(s) emitting an anti-germicidal radiation and/or antimicrobial radiation. The exemplary apparatus can be structured so that the at least one sole is exposed to the radiation.

The exemplary method can include automatically initiating an emission of the exemplary anti-germicidal radiation and/or the antimicrobial radiation after a predetermined amount of time passes from a time when the subject applies force on the apparatus, for example. The exemplary method also can include initiating an emission of the exemplary anti-germicidal radiation and/or antimicrobial radiation upon receiving a manual input from the subject, for example.

In addition, the exemplary method can include stopping the emission of the exemplary anti-germicidal radiation and/or antimicrobial radiation when a signal to stop is received by the radiation source(s). The exemplary signal can be based upon time and/or an indication from a sensor, for example. The exemplary method can include the exemplary sensor detecting a level of pathogens residing on at least one sole of the subject's footwear, and providing an indication when a threshold level has been reached indicating the level, for example. The exemplary method also can include a timer providing the exemplary signal to stop after a predetermined amount of time passes from a time when the emission of the exemplary anti-germicidal radiation and/or antimicrobial radiation is initiated. Additionally, the exemplary method can include generating the exemplary signal to stop when a malfunction of at least one part of the exemplary apparatus is detected and/or a need for maintenance of at least one part of the exemplary apparatus is detected, for example.

These and other objects, features and advantages of the present invention will become apparent upon reading the following detailed description of exemplary embodiments of the invention, when taken in conjunction with the appended claims.

BRIEF DESCRIPTION OF THE DRAWINGS

Further objects, features and advantages of the invention will become apparent from the following detailed description taken in conjunction with the accompanying Figures showing illustrative embodiments of the invention, in which.

Figure 1:
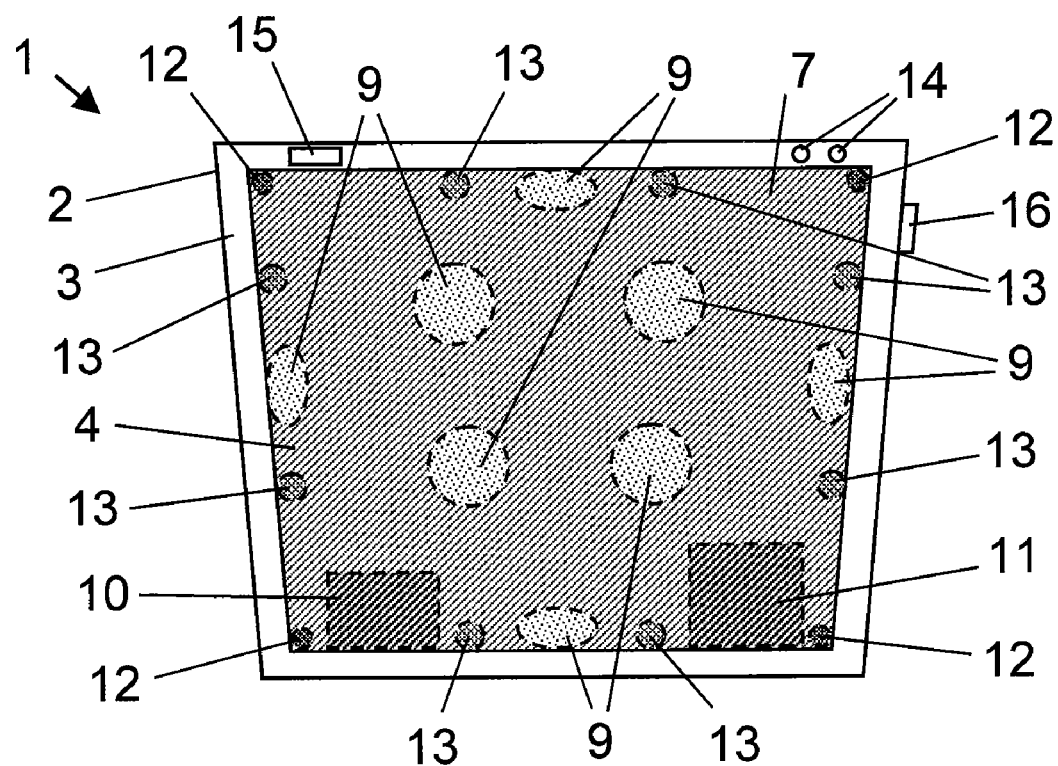
FIG. 1 is a top view of an exemplary embodiment of an apparatus according to the present invention that can significantly reduce and/or eliminate germs and/or bacteria from the soles of a person's footwear.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described exemplary embodiments without departing from the true scope and spirit of the subject invention as defined by the appended claims.

DETAILED DESCRIPTION OF EXEMPLARY EMBODIMENTS

FIG. 1 shows a top view of an exemplary embodiment of an apparatus according to the present invention that can significantly reduce and/or eliminate germs and/or bacteria from the soles of a person's footwear (e.g., including shoes, sandals, sneakers, flip-flops, etc.). The exemplary apparatus 1 includes a housing 2. In the exemplary embodiment shown in FIG. 1, housing 2 can be composed of a hard plastic material. However, any other suitable material can be used, including, e.g., ceramics, metal, steel, carbon-fiber, marble, wood, etc. The choice of the material can be so as to preferably be sufficiently strong so as to support a person weighing up to 300 lbs, for example, although it may also be beneficial for exemplary embodiments according to the present invention to support a person weighing up to 400 lbs, or more. It may also be preferable for the exemplary apparatus 1 to support a person weighing only up to 200 lbs, for example, particularly if such an embodiment is designed and manufactured to be smaller and/or lighter in weight than other exemplary embodiments of the present invention that are capable of supporting a greater amount of weight. One skilled in the art should understand the various benefits and concerns that should be taken into consideration in determining the type and quantity of material used to make housing 2 as well as the manufacturing techniques that may be employed to make it based on such choice of materials.

Housing 2 can include a decorative trim 3 that can extend around the perimeter of the top of housing 2, as shown in FIG. 1, for example. Trim 3 may have a width, for example, from about ⅛ of an inch to about 5 inches, and may preferably be from about 1 inch to about 2 inches in width. Trim 3 can be made of the same material as the housing or any other material that can be joined directly or indirectly to housing 2. As shown in FIG. 1, for example, trim 3 may preferably surround footpad 4.

One or more anti-germicidal and/or antimicrobial light sources 9 can be housed within the exemplary housing 2 of the exemplary apparatus 1. Anti-germicidal and antimicrobial light sources are generally known to one skilled in the art of using a type of the exemplary light for disinfecting objects used in a hospital, for example. It can be preferable for the exemplary anti-germicidal and/or antimicrobial light source (s) 9 to emit ultra-violet light and/or radiation ("UV") having an exemplary wavelength of about 250-400 nm, for example. It can also be beneficial for the exemplary UV wavelength to be about 260-360 nm, for example. However, any suitable UV wavelength can be used that will sufficiently disinfect (e.g. significantly reduce or eliminate pathogens) according to various exemplary embodiments of the present invention. Similarly, any other anti-germicidal and antimicrobial light source 9 can be employed according to various exemplary embodiments of the present invention, whether currently known or to be developed. Because exemplary embodiment 1 is structured to prevent such light from escaping from the interior of the apparatus except for that light applied to the soles of a person's footwear, the exemplary light source 9 with corresponding wavelengths can be selected so as to optimize disinfecting with minimal risk or no risk of such light coming in contact with a person's skin and thereby causing harm, for example. Examples of light and/or radiation sources may include, e.g., a UV light bulb, LED (light-emitting diode), radiation cone, etc.

The exemplary housing 2 can also include an exemplary power source 10 that is configured to provide sufficient power to drive the anti-germicidal and/or antimicrobial light source (s) 9, for example. According to various exemplary embodiments of the present invention, the exemplary power source 10 can also contain sufficient power to drive one or more a sensors and/or timers as well as one or more visible light indicators 14 and/or one or more audible sound indicators 15, for example. The exemplary one or more visible light indicators 14 and/or the exemplary one or more audible sound indicators 15 can be embedded within and/or attached to the exemplary trim 3, for example. Power can be provided via a standard AC outlet (i.e., 110V and/or 220V), for example. Alternatively, or in addition, a battery can provide power, and such battery may be charged when the exemplary apparatus is plugged in to a power outlet, for example.

One or more exemplary sensors and/or timers 12 can be included in the exemplary housing 2 for determining when the soles of the footwear of a person using the exemplary apparatus 1 are sufficiently disinfected. For example, after a particular time period, one or more signals can be transmitted to turn off the anti-germicidal and/or antimicrobial light source(s) 9, and alert the person using the exemplary apparatus 1 that the disinfecting process is complete and they may thus step off of the exemplary apparatus 1. Such exemplary signals can be sent directly from the exemplary sensor and/or timer 12 or by an electronic circuit or control unit 11 included in the exemplary apparatus 1, for example.

Various types of sensors can be used as the one or more exemplary sensors 12 to measure the level of pathogens according to exemplary embodiments of the present invention. Such sensors are generally known to those skilled in the art of detecting and measuring pathogens, such as various medical professionals and lab technicians, for example. Exemplary devices for alerting a person when the disinfecting process is complete can include one or more exemplary visible light indicators 14 and/or one or more exemplary audible sound indicators 15, for example. Such exemplary visible light indicator(s) 14 can be one or more LEDs, for example. The exemplary audible sound indicator(s) 15 may be an electronically generated audible signal, for example. Exemplary embodiments according to the present invention also may be structured to detect and alert a user when a light source needs replacing or if a problem or some type of malfunction has occurred.

One or more weight scales and/or pressure sensors 13 can be included in the exemplary housing 2. The exemplary anti-germicidal and/or antimicrobial light source(s) 9 may automatically be turned on after a specific amount of time after the one or more weight scales and/or pressure sensors 13 detect an amount of weight (or, e.g., force, pressure) greater than and/or equal to a threshold being applied on foot plate 5, for example. The amount of time can preferably be at least the amount of time it takes for a person of a specific weight to sink through the exemplary gel 8 and come to rest on the exemplary bottom portion 6, thereby displacing the exemplary gel 8. A processor or the exemplary control unit 11 can determine the least amount of time, and preferably add thereto about 1-10 seconds, before activating the exemplary light source(s) 9, for example. Adding about 2-5 seconds to the calculated amount of time may also be beneficial, for example. The threshold of weight can preferably be about 30 lbs-100 lbs, for example. According to various embodiments of the present invention, it also may be beneficial for the threshold weight to be about 50 lbs-70 lbs, for example. Alternatively, or in addition, an exemplary switch and/or button 16 can be provided to allow a person to activate the exemplary light source(s) 9 manually. An exemplary switch and/or button 16 can be placed directly on the exemplary housing 2 and/or be housed in a remote unit that can be connected to and/or in communication with the exemplary control unit 11 via a tethered wire or wireless communication, such as, e.g., Blue Tooth™, for example.

Figure 2:
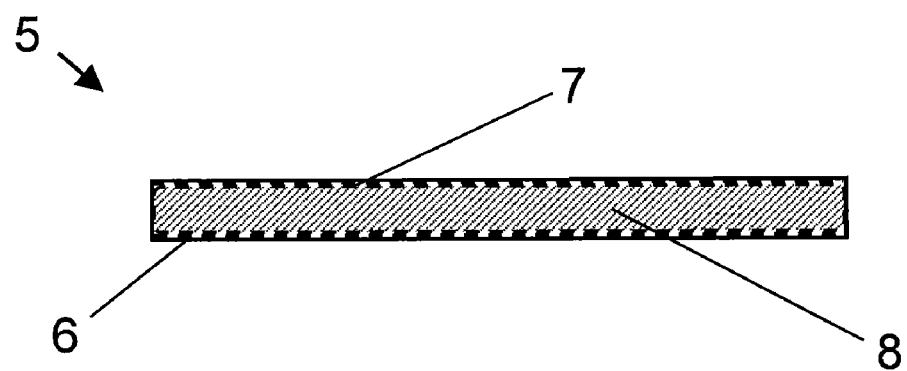
FIG. 2 is front view of the exemplary embodiment of the apparatus shown in FIG. 1, showing a foot plate according to an exemplary embodiment according to the present invention.

As shown in FIG. 2, the exemplary footpad 4 can include an exemplary footplate 5, for example, which includes a bottom portion 6 and a top portion 7. The exemplary bottom portion 6 can preferably be composed of a hard Plexiglas, for example, although any suitable transparent material can be used according to exemplary embodiments of the present invention. Similarly to the exemplary apparatus 1, the exemplary bottom portion 6 can be dimensioned to have sufficient strength to support a person weighing up to about 300 lbs, for example, although it may also be beneficial for exemplary embodiments according to the present invention to support a person weighing up to about 400 lbs, or more. It may also be preferable for the exemplary bottom portion 6 to support a person weighing only up to about 200 lbs, for example, particularly if such an embodiment is designed and manufactured to be used in a smaller and/or lighter weight apparatus than other exemplary embodiments of the present invention.

According to the exemplary embodiment shown in FIG. 2, the exemplary top portion 7 can be made from a soft plastic material that is substantially transparent at least when it is in a stretched state, for example. When the exemplary apparatus 1 is not being used by a person, the exemplary top portion 7 resides substantially flat and/or within the same plane near the top of foot plate 5 in a relaxed (or unstretched) state. The exemplary bottom portion 6 and the exemplary top portion 7 can, together with the internal vertical sides of the exemplary housing 2, provide a substantially or completely sealed space. A gel 8 can be provided in such space between the exemplary bottom portion 6 and the exemplary top portion 7, for example. The exemplary gel 8 can be opaque and of a consistency that can facilitate it to be displaced by a person weighing at least 50 lbs, for example, when such person is standing on top of the exemplary top portion 7 on top of the exemplary gel 8. However, it may be beneficial, according to exemplary embodiments of the present invention, to utilize the exemplary gel 8 to be displaced by a person weighing at least 30 lbs, for example, or only by a person weighing at least 100 lbs, for example. The exemplary gel 8 can be made of a silicone-based material, for example, although any suitable material can be used with various embodiments of the present invention.

Figure 3:
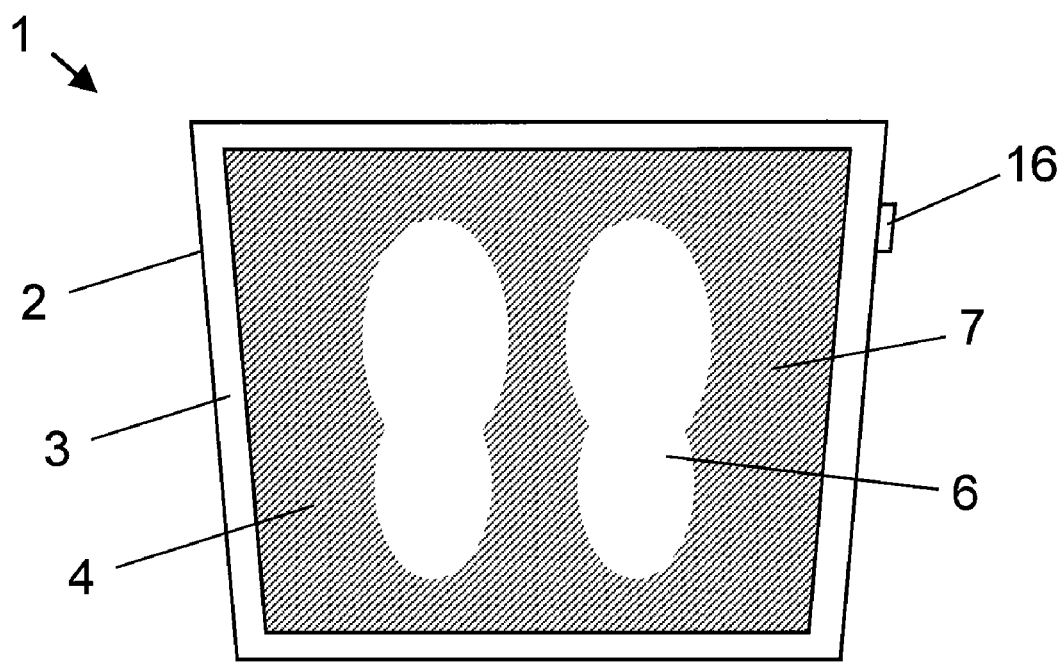
FIG. 3 is another top view of the exemplary embodiment of the apparatus shown in FIGS. 1 and 2, appearing as it may when being used by a person.

As shown in FIG. 3, when apparatus 1 is being used by a person, the exemplary top portion 7 can be stretched so as to allow the person standing on the exemplary footpad 4 (e.g. on the exemplary top portion 7 of the exemplary foot plate 5) to sink through the exemplary gel 8 so that his or her weight displaces the exemplary gel 8 around their footwear and the soles of their footwear come to rest and be supported by the exemplary top portion 7 resting directly on top of the exemplary bottom portion 6, for example. As a result, the exemplary footplate 5 can be opaque, except for the area of the exemplary footplate 5 in which the exemplary gel 8 has been displaced by the footwear of the person using the exemplary apparatus 1, for example. This exemplary embodiment facilitates utilization of the anti-germicidal and/or antimicrobial light to substantially reduce and/or eliminate pathogens residing on the sole of a person's footwear by emitting the anti-germicidal and/or antimicrobial light, e.g., only on the soles of the person's footwear (and/or sides thereof). Because the exemplary opaque gel 8 is displaced so as to surround the person's footwear, and the rest of the exemplary foot plate 5 is opaque due to the exemplary gel 8, the emitted anti-germicidal and/or antimicrobial light would likely be prevented from escaping from the interior of apparatus 1.

Figure 4:
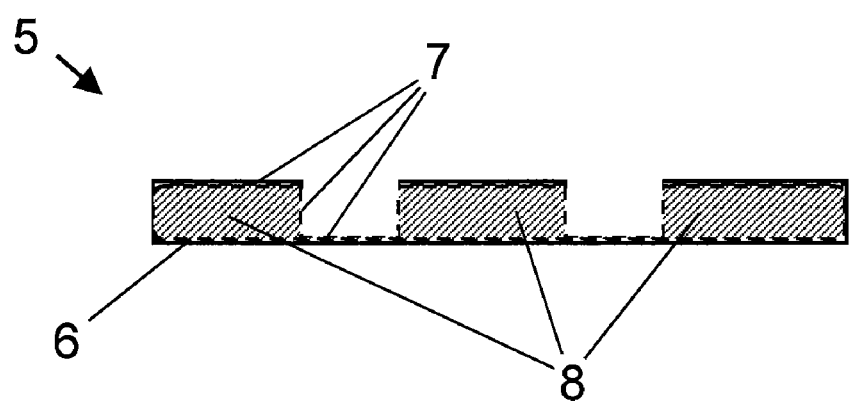
FIG. 4 is a front view of an exemplary foot plate according to an exemplary embodiment of the apparatus shown in FIGS. 1-3, appearing as it may when being stepped into by a person.

FIG. 4 is a front view of the exemplary footplate 5 according to the exemplary embodiment of the apparatus shown in FIGS. 1-3, appearing as it may when being stepped into by a person, for example. The exemplary top portion 7 is shown in a stretched state so as to allow the person standing on the exemplary footpad 4 (e.g., on the exemplary top 7 of the exemplary footplate 5) to sink through the exemplary gel 8 so that his/her weight displaces the exemplary gel 8 around their footwear and the soles of their footwear come to rest and be supported by the exemplary top portion 7 resting directly on the top of the exemplary bottom portion 6, for example. As discussed above with respect to FIG. 3, the result is that the exemplary footplate 5 can be opaque, except for the area of the exemplary footplate 5 in which the exemplary gel 8 has been displaced by the footwear of the person using the exemplary apparatus 1, for example. This exemplary embodiment facilitates the utilization of the one or more anti-germicidal and/or antimicrobial light to substantially reduce and/or eliminate pathogens residing on the sole of a person's footwear by emitting the anti-germicidal and/or antimicrobial light, e.g., only on the soles of the person's footwear (and/or sides thereof). Because the exemplary opaque gel 8 is displaced so as to surround the person's footwear, and the rest of the exemplary foot plate 5 is opaque due to the exemplary gel 8, the emitted anti-germicidal and/or antimicrobial light would likely be prevented from escaping from the interior of the exemplary apparatus 1. Thus, the risk of such light harming a person's skin when the exemplary apparatus 1 is properly configured and used, for example, is minimized and/or eliminated.

Figure 5:
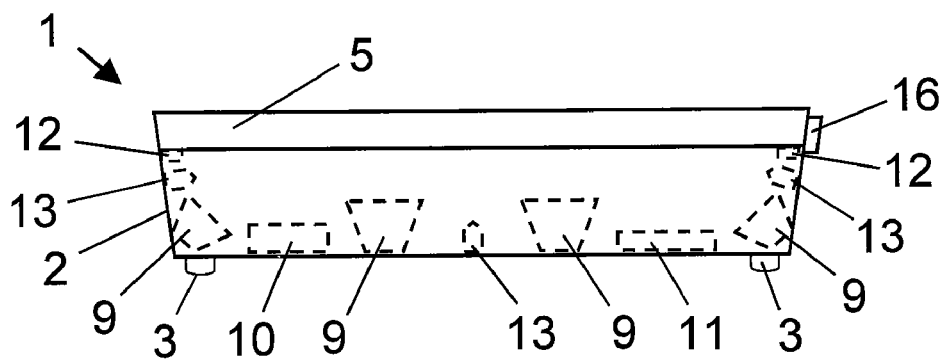
FIG. 5 is a side view of the exemplary embodiment of the apparatus shown in FIGS. 1-4.

FIG. 5 is a side view of the exemplary embodiment of the apparatus shown in FIGS. 1-4. The exemplary footplate 5 is shown in FIG. 5 as being provided at the top of housing 2. Shocks and/or feet 9 can be provided on the underside of the bottom of the exemplary housing 2, as shown in FIG. 5, for example. The exemplary shocks and/or feet 9 can be made of rubber, for example, to provide cushioning and anti-slip properties. Other exemplary embodiments of the present invention can utilize shocks that can include compression springs, for example. Wheels, rollers or gliders could also be provided on the bottom of shocks and/or feet 9 according to various exemplary embodiments of the present invention.

Although only two exemplary shocks and/or feet 9 can be seen in FIG. 5, there may be, e.g., four or more according to the illustrated exemplary embodiment, e.g., one in or near each corner of the housing (or equally spaced if the housing is alternatively shaped as, e.g., an ellipse). Various exemplary embodiments of the present invention can include a different number of shocks and/or feet 9, such as, e.g., 3-10 thereof, although, 4-6 thereof may be preferable to provide proper stability and support to a person standing on the exemplary apparatus 1.

Figure 6A:
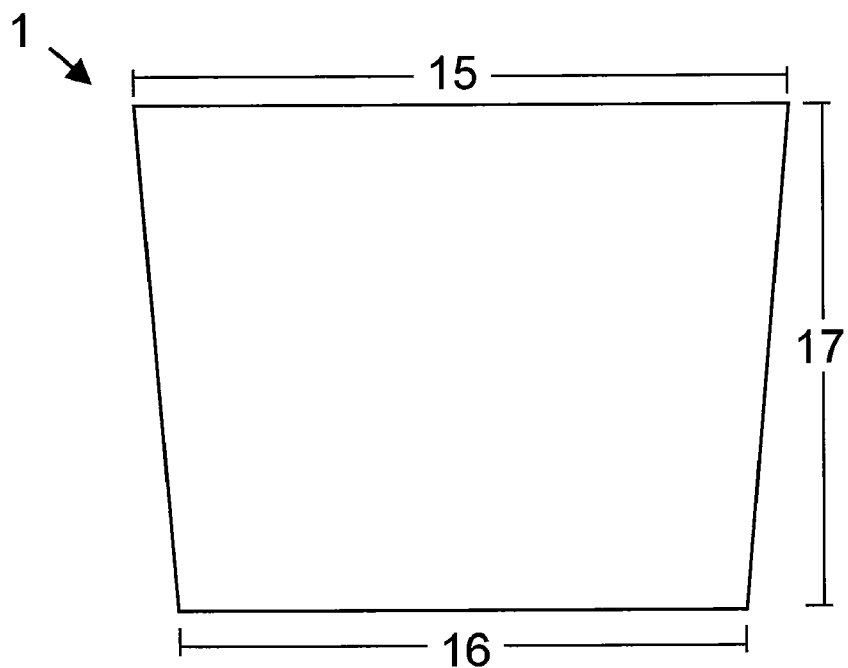
FIG. 6a is a another top view and FIG. 6b is another side view of the exemplary embodiment of the apparatus shown in FIGS. 1-5, showing exemplary dimensions of the exemplary apparatus.
Figure 6B:
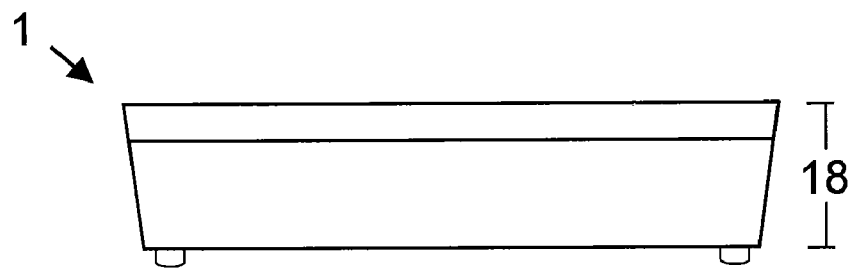

FIG. 6a is a another top view and FIG. 6b is another side view of the exemplary embodiment of the apparatus shown in FIGS. 1-5, illustrating exemplary dimensions of the exemplary apparatus 1. Similarly to the view shown in FIG. 5, the exemplary footplate 5 is shown in FIG. 6b as residing at the top of the exemplary housing 2 and the exemplary shocks and/or feet 9 are shown as being provided on the underside of the bottom of the exemplary housing 2. The exemplary dimensions of the exemplary apparatus 1 may be large enough to house the exemplary footplate 5, the one or more exemplary anti-germicidal and/or antimicrobial light sources 9, and the other exemplary components discussed herein, and provide stability for a person to safely stand thereon. However, the exemplary dimensions of the exemplary apparatus 1 may also be set to be sufficiently small so as to not be obtrusive when placed near the interior and/or exterior of a doorway to a dwelling or building, and so the exemplary apparatus 1 can be moved and/or carried by a person.

For example, an exemplary front width 17 can be about 18-30 inches, although about 22-26 inches may be beneficial. An exemplary rear width 18 can be about 14-24 inches, although about 18-22 inches may be beneficial. An exemplary depth 19 can be about 10-18 inches, although a range of 12-16 inches may be preferable. An exemplary height 20 can be as low as possible but still large enough so as to accommodate the exemplary footplate 5, the light source(s) 9, and other exemplary components discussed herein. However, a height of about 2-6 inches may be preferable, although a height in the range of 3-5 inches also may be beneficial.

The foregoing merely illustrates the principles of the invention. Various modifications and alterations to the described exemplary embodiments will be apparent to those skilled in the art in view of the teachings herein. It will thus be appreciated that those skilled in the art will be able to devise numerous devices, arrangements and methods which, although not explicitly shown or described herein, embody the principles of the invention and are thus within the spirit and scope of the present invention. The detailed description, given by way of example, but not intended to limit the invention solely to the specific exemplary embodiments described, may best be understood in conjunction with the accompanying Figures.

What is claimed is:

1. An apparatus for at least one of reducing or eliminating at least one of germs or bacteria from at least one sole of a footwear of a subject, comprising:
   a housing; and
   a first particular part located within or coupled to the housing and including at least one first radiation source and at least one second radiation source, wherein at least one of the first or second radiation sources is exposed to irradiate the at least one sole when the subject applies force on the apparatus, and wherein the at least one second radiation source includes a structure which is provided below a plane on which the at least one sole is intended to be placed, and configured to emit at least one of an anti-germicidal radiation or an antimicrobial radiation in a non-orthogonal direction directly to an upper portion of the housing.

2. The apparatus recited in claim 1, wherein the at least one of the anti-germicidal radiation or the antimicrobial radiation is at least one of an ultra-violet light or radiation.

3. The apparatus recited in claim 1, further comprising a second particular part located at or near a top section of the housing, wherein the second particular part includes (i) a top portion, (ii) a bottom portion, and (iii) a gel disposed therebetween.

4. The apparatus recited in claim 3, wherein the bottom portion is at least substantially transparent.

5. The apparatus recited in claim 3, wherein the gel is at least substantially opaque.

6. The apparatus recited in claim 3, wherein the top portion sinks to the bottom portion so as to displace the gel under the subject's footwear when the subject steps onto the top portion.

7. The apparatus recited in claim 3, wherein the at least one radiation source is configured to automatically initiate an emission of the at least one of the anti-germicidal radiation or the antimicrobial radiation after a predetermined amount of time passes from a time when the subject applies force on the second particular part.

8. The apparatus recited in claim 1, wherein the at least one radiation source is configured to initiate an emission of the at least one of the anti-germicidal radiation or the antimicrobial radiation upon receiving a manual input from the subject.

9. The apparatus recited in claim 1, wherein the at least one radiation source is configured to emit the at least one of the anti-germicidal radiation or the antimicrobial radiation until a signal to stop is received thereby.

10. The apparatus recited in claim 9, wherein the signal is based upon at least one of a time or an indication from a sensor provided in or coupled to the housing.

11. The apparatus recited in claim 10, wherein the sensor is configured to (i) detect a level of pathogens residing on the soles of the subject's footwear, and (ii) provide the indication when a threshold level has been reached indicating the level.

12. The apparatus recited in claim 1, wherein the at least one radiation source is at least one of a radiation cone, UV light bulb or LED.

* * * * *